US005605687A

United States Patent [19]
Lee

[11] Patent Number: 5,605,687
[45] Date of Patent: Feb. 25, 1997

[54] METHODS AND COMPOSITIONS OF A POLYMER (POLOXAMER) FOR REPAIR OF ELECTRICAL INJURY

[75] Inventor: Raphael C. Lee, Chicago, Ill.

[73] Assignee: Arch Development Corporation, Chicago, Ill.

[21] Appl. No.: 461,255

[22] Filed: Jun. 5, 1995

Related U.S. Application Data

[63] Continuation of Ser. No. 884,429, May 15, 1992, abandoned.

[51] Int. Cl.[6] .......................... A61K 9/06; A61K 9/12; A61K 31/77
[52] U.S. Cl. .................. 424/78.06; 424/78.37; 424/423; 424/DIG. 13
[58] Field of Search .................. 424/78.37, DIG. 13, 424/423, 78.06

[56] References Cited

U.S. PATENT DOCUMENTS

| 29,909 | 2/1879 | Kartz | 252/89 |
|---|---|---|---|
| 2,674,619 | 4/1954 | Lundsted | 260/485 |
| 2,854,378 | 11/1958 | Buckwalter | 167/64 |
| 3,089,818 | 5/1963 | Stone | 167/65 |
| 3,140,232 | 7/1964 | Noseworthy | 167/65 |
| 3,422,186 | 1/1969 | Sasmor et al. | 424/79 |
| 3,577,522 | 5/1971 | Hymes | 436/78 |
| 3,590,125 | 6/1971 | Hymes | 424/78 |
| 3,641,240 | 2/1972 | Hymes | 434/78 |
| 3,740,421 | 6/1973 | Schmolka | 424/65 |
| 3,867,521 | 2/1975 | Miskel et al. | 424/37 |
| 3,956,259 | 5/1976 | Garcia et al. | 260/112 |
| 3,980,772 | 11/1976 | Ginger et al. | 424/94 |
| 4,073,886 | 2/1978 | Kehm | 260/112 |
| 4,100,271 | 7/1978 | Krezanoski | 424/78 |
| 4,105,650 | 8/1978 | Shanbrom et al. | 260/112 |
| 4,179,337 | 12/1979 | Davis et al. | 435/181 |
| 4,186,253 | 1/1980 | Yokoyama et al. | 436/240 |

(List continued on next page.)

FOREIGN PATENT DOCUMENTS

| 43628/68 | 11/1968 | Australia . |
|---|---|---|
| 0200467A3 | 4/1986 | European Pat. Off. . |
| WO87/06831 | 11/1987 | European Pat. Off. . |
| WO87/06836 | 11/1987 | European Pat. Off. . |
| 2267112 | 4/1975 | France . |
| 1930957 | 6/1969 | Germany . |
| 840155 | 7/1960 | United Kingdom . |
| WO8502116 | 5/1985 | WIPO . |

OTHER PUBLICATIONS

Aldwinckle et al., "Effects of Poly(Ethylene Glycol) on Liposomes and Erythrocytes: Permeability Changes and Membrane Fusion," *Biochimica et Biophysica Acta*, 689:548–560, 1982.

Arnold et al., "The Dielectric Properties of Aqueous Solutions of Poly(Ethylene Glycol) and Their Influence on Membrane Structure," *Biochimica et Biophysica Acta*, 815:515–518, 1985.

Arnold et al., "Effect of Poly(Ethylene Glycol) on Phospholipid Hydration and Polarity of the External Phase," *Biochimica et Biophysica Acta*, 728:121–128, 1983.

(List continued on next page.)

*Primary Examiner*—Edward J. Webman
*Attorney, Agent, or Firm*—Arnold, White & Durkee

[57] ABSTRACT

Novel methods for the treatment of tissue damage resulting from cell membrane permeabilization due to electrical injury are disclosed. Such methods include treatment with a surface active copolymer which is herein shown to promote membrane repair. The administration of Poloxamer 188 is shown to reduce tissue inflammation and damage following electrical injury in vivo. Also disclosed are methods for the treatment of cell and tissue damage after electrical injury using a surface active copolymer in combination with a high energy phosphate compound capable of recharging cellular energy stores and potentiating cell repair and survival. Compositions comprising surface active copolymers for intravenous, intramuscular, and topical use are also disclosed, along with novel compositions comprising a combination of a surface active copolymer and a high energy phosphate compound.

10 Claims, 6 Drawing Sheets

U.S. PATENT DOCUMENTS

| | | | |
|---|---|---|---|
| 4,305,922 | 12/1981 | Rhodes | 424/1 |
| 4,395,393 | 7/1983 | Schmolka | 424/78 |
| 4,407,790 | 10/1983 | Oakes et al. | 424/78 |
| 4,474,753 | 10/1984 | Haslam et al. | 424/78.06 |
| 4,600,652 | 7/1986 | Solomon et al. | 428/423 |
| 4,609,546 | 11/1986 | Hirstaal | 424/83 |
| 4,801,452 | 1/1989 | Hunter et al. | 424/94.63 |
| 4,837,014 | 6/1989 | Hunter et al. | 424/94.63 |
| 4,873,083 | 10/1989 | Hunter et al. | 424/83 |
| 4,879,109 | 11/1989 | Hunter | 424/83 |
| 4,897,263 | 1/1990 | Hunter | 424/83 |
| 4,937,070 | 6/1990 | Hunter | 424/83 |
| 4,997,664 | 3/1991 | Hunter | 424/83 |
| 5,002,965 | 3/1991 | Ramwell et al. | 514/468 |
| 5,017,370 | 5/1991 | Hunter | 424/83 |
| 5,028,599 | 7/1991 | Hunter | 424/83 |
| 5,030,448 | 7/1991 | Hunter | 424/83 |
| 5,032,394 | 7/1991 | Hunter | 424/83 |
| 5,039,520 | 8/1991 | Hunter | 424/83 |
| 5,041,288 | 8/1991 | Hunter | 424/83 |
| 5,045,468 | 9/1991 | Darfler | 435/240.31 |
| 5,047,236 | 9/1991 | Hunter et al. | 424/83 |
| 5,064,643 | 11/1991 | Hunter et al. | 424/83 |
| 5,071,649 | 12/1991 | Hunter | 424/78.38 |
| 5,075,333 | 12/1991 | Bryce et al. | 514/481 |
| 5,078,995 | 1/1992 | Hunter et al. | 424/78.38 |
| 5,080,894 | 1/1992 | Hunter et al. | 424/78.38 |
| 5,089,260 | 2/1992 | Hunter et al. | 424/78.38 |
| 5,152,979 | 10/1992 | Hunter | 424/78.38 |
| 5,177,065 | 1/1993 | Silvetti, Sr. et al. | 424/70 |

OTHER PUBLICATIONS

Bahnson & Boggs, "Addition of Serum to Electroporated Cells Enhances Survival and Transfection Efficiency," *Biochemical and Biophysical Research Communications*, 171(2):752–757, 1990.

Behr et al., "Efficient Gene Transfer Into Mammalian Primary Endocrine Cells with Lipopolyamine–Coated DNA," *Proceedings of the National Academy of Science USA*, 86:6982–6986, 1989.

Boni et al., "Lipid–Polyethylene Glycol Interactions: I. Induction of Fusion Between Liposomes," *Journal of Membrane Biology*, 62:65–70, 1981.

Boni et al., "Lipid–Polyethylene Glycol Interactions: II. Formation of Defects in Bilayers," *Journal of Membrane Biology*, 62:71–77, 1981.

Chaudry et al., "ATP–MgCl$_2$ Infusion in Man: Increased Cardiace Output Without Adverse Systemic Remodynamic Effects," *Surgical Forum*, 35:14–16, 1984.

Chaudry et al., "Effect of Adenosine Triphosphate–Magnesium Chloride Administration in Shock,"*Surgery*, 75(2):220–227, 1974.

Gaehtgens & Benner, "Desaggregation of Human Red Blood Cells by Various Surface–Active Agents as Related to Changes of Cell Shape and Hemolysis," *Acta Haemat.*, 53:82–89, 1975.

Hirasawa et al., "Improved Survival and Reticuloendothelial Function with Intravenous ATP–MgCl$_2$ Following Hemorrhagic Shock," *Circulation Shock*, 11(2):141–148, 1983.

Janoff et al., "The Modification of Human Erythrocyte Membrane Structure by Membrane Stabilizers: An Electron Sprin Resonance Study," *American Journal of Hematology*, 10:171–179, 1981.

Knize et al., "Use of Antisludging Agents in Experimental Cold Injuries," *Surgery, Gynecology & Obstetrics*, 129:1019–1026, 1969.

Loeffler et al., "Lipopolyamine–Mediated Transfection Allows Gene Expression Studies in Primary Neuronal Cells," *Journal of Neurochemistry*, 54(5):1812–1815, 1990.

McNeil, "Cell Wounding and Healing," *American Scientist*, 79:222–235, 1991.

Minetti et al., "Interaction of Neutral Polysaccharides with Phosphatidylcholine Multilamellar Liposomes. Phase Transitions Studied by the Binding of Fluorescein–Conjugated Dextrans," *Biochemistry*, 18(12):2541–2548, 1979.

Papahadjopoulos et al., "Molecular Mechanisms of Calcium–Induced Membrane Fusion," *Journal of Bioenergetics and Biomembranes*, 22(2):157–179, 1990.

Peters, "Biology of Radiation Therapy," *In Comprehensive Management of Head and Neck Tumors*, Eds., S.E. Thawley & W. R. Panje, W. B. Saunders Company, 1:132–152, 1987.

Rols & Teissié, "Electropermeabilization of Mammalian Cells: Quantitative Analysis of Phenomenon" *Biophysical Journal*, 58:1089–1098, 1990.

Sáez et al., "Detergent–Like Properties of Polyethyleneglycols in Relation to Model Membranes," *FEBS Letters*, 137(2):323–326, 1982.

Schmolka, "A Review of Block Polymer Surfactants," *Journal of the American Oil Chemists' Society*, 54:110–116, 1977.

Sowers, "The Mechanism of Electroporation and Electrofusion in Erythrocyte Membranes," In: *Electroporation and Electrofusion in Cell Biology*, Neumann et al. eds., Plenum Publishing Corporation, pp. 229–256, 1989.

Tsong, "Electroporation of Cell Membranes," *Biophysical Journal*, 60:297–306, 1991.

Wang et al., "ATP–MgCl$_2$ Restores the Depressed Hepatocellular Function and Hepatic Blood Flow Following Hemorrhage and Resuscitation," *Journal of Surgical Research*, 50(4):368–374, 1991.

The Scientific Basis for the Biologic Activities of RheothRx™ Copolymer: A Rheologic, Antithrombotic and Cytoprotective Preparation, CytRx® Corporation.

Lee et al., "Surfactant Induced Sealing of Electropermeabilized Skeletal Muscle Membranes In Vivo," *Proceedings of the National Academy of Sciences*, 89(10):4524–4528, 1992.

Weatherley–White et al., "Experimental studies in cold injury, V. Circulatory hemodynamics", *Surgery* (1969) 66(1):208–214.

Marquis et al., "Agitation and aeration effects in suspension mammalian cell cultures", *Cytotechnology* (1989) 2:163–170.

Slepnev et al., "Micelles of Poly(oxyethylene)–Poly(oxypropylene) Block Copolymer (Pluronic) as a Tool for Low–Molecular Compound Delivery into a Cell: Phosphorylation of Intracellular Proteins with Micelle Incorporated [$\gamma$-$^{32}$P]ATP$^1$", *Biochemistry International*, (1992) 26(4):587–595.

Benner et al., "Uber die Wirkung von Pluronic F68, einem Polyoxypropylen–Polyoxyathylen–Kondensat, auf die ADP–induzierte Thrombocytenaggregation in vitro," *Pfungers Arch.*, 315:45–52, 1970.

Benner and Brunner, "Cold–Induced Platelet Aggregation In Vivo and its Inhibition by a Nonionic Surface Active Substance," *Thrombosis Research*, 2:331–342, 1973.

Block et al., "Acutely Traumatized Canine Ureter," *Urology*, III(2):190–194, 1974.

Sugi et al., "The Use of Fluosol(TM)–DA 20% (FDA) in Emergency Situations: A Report of 67 Clinical Cases," (Abstract), International Symposium on Advances in Blood Substitute Research, San Francisco, California, Sep. 29–Oct. 1, 1982, Alan R. Liss, Inc., New York.

Ceresa, "The Application of Block Copolymer Polyol Surfactants," *Block and Graft Copolymerization*, 2:174–272, 1976.

Chesebro et al., "Restenosis After Arterial Angioplasty: A Hemorheologic Response to Injury," *Am. J. Cardiol.*, 60:10B–16B, 1987.

Danielson et al., "of Pluronic F–68 to Diminish Fat Emboli and Hemolysis During Cardiopulmonary Bypass," *The Journal of Thoracic and Cardiovascular Surgery*, 59(2):178–184, 1970.

Divertie and Petty, "Adult Respiratory Distress Syndrome," *Current Concepts*.

Forman et al., "Beneficial Long–Term Effect of Intracoronary Perfluorochemical on Infarct Size and Ventricular Function in a Canine Reperfusion Model," *JACC*, 9(5):1082–1090, 1987.

Forman et al., "Reduction of infarct size with intracoronary perfluorochemical in a canine preparation of reperfusion," *Circulation*, 71(5):1060–1068, 1985.

Geyer, "Potential uses of artificial blood substitutes," *Federation Proceedings*, 34(6):1525–1528, 1975.

Goodman et al., "Perfluorocarbon Emulsions in Cancer Therapy: Preliminary Observations on Presently Available Formulations," *Int. Biol. Phys.*, 10:1421–1424, 1984.

Grover et al., "The Effect of Pluronic F–68 on Circulatory Dynamics and Renal and Carotid Artery Flow During Hemorrhagic Shock," *Journal of Surgical Research*, 17:30–35, 1974.

Grover et al., "A Nonionic Surfactant and Blood Viscosity," *Arch. Surg.*, 106:307–310, 1973.

Grover et al., "Beneficial Effect of Pluronic F–68 on the Microcirculation in Experimental Hemorrhagic Shock," *Surgical Forum*, 30–32.

Harjula et al., "Perfluorocarbon Solution as a Myocardial Preservative," *Journal of Applied Cardiology*, 2(2):121–136, 1987.

Heron and Paton, "A Method for Measuring a Nonionic Surface–Active Agent (Pluronic F–68) in Biological Fluids," *Analytical Biochemistry*, 24:491–495, 1968.

Heinz et al., "Short– and Long–term Changes in Myocardial Perfusion After Percutaneous Transluminal Coronary Angioplasty Assessed by Thallium–201 Exercise Scintigraphy," *Circulation*, 63(5):1001–1007, 1981.

Hoie and Schenk, "Effects of Pluronic F 68, Poloralkol, on Vascular Resistance In Vivo," *Journal of Surgical Research*, 11(10):515–517, 1971.

Hymes et al., "Influence of an industrial surfactant (pluronic F–68) on human amniotic fluid embolism," *Amer. J. Obstet. Gynec.*, 107(8):1217–1222, 1970.

Hymes et al., "The Influence of an Industrial Surfactant Pluronic F–68 in the Treatment of Hemorrhagic Shock," *Journal of Surgical Research*, 11(4):191–197, 1971.

Justice et al., "Prevention of Thrombosis with Agents Which Reduce Platelet Adhesiveness," *The American Surgeon*, 186–189, 1974.

Kanter et al., "Superiority of Perfluorocarbon Cardioplegia Over Blood or Crystalloid Cardioplegia," *Circulation*, 64(II):76–80, 1987.

Katzenstein et al., "Diffuse Alveolar Damage–The Role of Oxygen, Shock and Related Factors," *American Journal of Pathology*, 85(1):210–224, 1976.

Ketchum et al., "Experimental Use of Pluronic F–68 in Microvascular Surgery," *Plastic & Reconstructive Surgery*, 53(3):288–292, 1974.

Ketchum, "Pharmacological alternations in the clotting mechanism: Use in microvascular surgery," *The Journal of Hand Surgery*, 3(5):407415, 1978.

Kunicki et al., "A Study of Variables Affecting the Quality of Platelets Stored at 'Romm Temperature'," *Transfusion*, 15(5):414–422, 1975.

Lane and Krukonis, "Reduction in the toxicity of a component of an artificial blood substitute by supercritical fluid fractionation," *Transfusion*, 28(4):375–378, 1988.

McBride et al., "Restenosis after Successful Coronary Angioplasty," *The England Journal of Medicine*, 318(6):1734–1737, 1988.

Moore et al., "Reduction of Splenic Vascular Resistance During Perfusion by Pluronic F68," *Journal of Surgical Research*, 8(12):563–566, 1968.

Murray et al., "An Expanded Definition of the Adult Respiratory Distress Syndrome," *Am. Rev. Respir. Dis.*, 138:720–723, 1988.

Naito and Yokoyama, "Perfluorochemical Blood Substitutes FC–43 Emulsion Fluosol–DA, 20% and 35%," *Technical Information* 5:1–176, 1978.

Padilla et al., "Effect of fluorocarbon emulsions on the mechanical fragility of normal and sickle cells: in vitro studies," *Federation Proceedings*, 34(8):1510–1512, 1975.

Paton et al., "The Use of a Nonionic Detergent Added to Organ Perfusates," *Organ Perfusion and Preservation*, 105–120, Date??.

Prida et al., "Percutaneous Transluminal Coronary Angioplasty in Evolving Acute Myocardial Infarction," *The American Journal of Cardiology*, 57:1069–1074, 1986.

Reindorf et al., "Perfluorocarbon Compounds: Effects on the Rheological Properties of Sickle Erythrocytes In Vitro," *American Journal of Hematology*, 19:229–236, 1985.

Repine et al., "Pulmonary Oxygen Toxicity and Ischemia–Reperfusion Injury," *Am. Rev. Respir. Dis.*, 136:483–485, 1987.

Richard and Sanders, "Effect of Lysine and Wetting Agents on Activated Plasminogen Solutions," *Canadian Journal of Biochemistry and Physiology*, 41:211–217, 1963.

Rodeheaver et al., "Pluronic F–68: A Promising New Skin Wound Cleanser," *Ann. Emerg. Med.*, 9(11):572–576, 1980.

Schmolka, "Artificial Skin I. Preparation and Properties of Pluonic F–127 Gels for Treatment of Burns," *J. Biomed. Mater. Res.*, 6:571–582, 1972.

Schwartz et al., "Aspirin and Dipyridamole in the Prevention of Restenosis after Percutaneous Transluminal Coronary Angioplasty," *The New England Journal of Medicine*, 318(26):1714–1719, 1988.

Smillie et al., "Cryopreservation of Human Platelet with Polyvinylpyrrolidone," *Transfusion*, 21(5):552–556, 1981.

Smith et al., "Pluronic F–68, A non–ionic emulsifier, reduces the adhesivity of liganded sickle erythrocytes," 6th *Int. Congress Biorheology Abstracts*, 23(3):238.

Spiess et al., "Protection from with Perfluorocarbons in Rabbits," *Stroke*, 17(6):1146–1149, 1986.

Thimas and Lamkin, "Paralysis of Phagocyte Migration Due to an Artificial Blood Substitute," *Bood*, 64(2):400–405, 1984.

Tokioka et al., "Effects of intracoronary infusion of arterial blood or Fluosol–DA 20% on regional myocardial metabolism and function during brief coronary artery occlusions," *Circulation*, 75(2):473–481, 1987.

Uno et al., "Determination of Surface–active Agents. Infrared Determination of the Proportion of Ethylene Oxide in Pluronic," *Chem. Pharm. Bull.*, 15(1):77–82, 1987.

Vasko et al., "Poloxalkol Pluronic F–68: A Priming Solution for Cardiopulmonary Bypass,".

Vercellott et al., "Activation of Plasma Complement by Perfluorocarbon Artificial Blood: Probable Mechanism of Adverse Pulmonary Reactions in Treated Patients and Rationale for Corticosteroid Prophylaxis," *Blood*, 59(6):1299–1304, 1982.

Williams Jr. et al., "Modulation of Rat Granulocyte Traffic by a Surface Active Agent in Vitro and Bleomycin Injury," *Proceedings of the Society for Experimental Biology and Medicine*, 188:461–470, 1988.

Tabuchi et al., "Use of Fluosol (TM) –DA 20% (FDA) as a Perfusate to Prevent Ischemic GI Damage," (Abstract), International Symposium on Advances in Blood Substitute Research, San Francisco, California, Sep. 29–Oct. 1, 1982, Alan R. Liss, Inc., New York.

Research News, "Perfluorochemical Emulsions: Promising Blood Substitutes, " *Science*, 179:669–672, 1973.

Pluronic & Tetronic Block Copolymer Surfactants, BASF Technical Brochure, 1989.

Ohta, Hiromichi, et al., "The Long Term Effects of Percutaneous Transluminal Angioplasty for Treating Patients with Renovascular Hypertension: Case Studies," *The Journal of Vascular Diseases*, 535–542, 1986.

"Pilot studies on the safety of PFC emulsion", 39–176, (author & journal unknown).

Aldwinclke et al., "Effects of Poly(Ethylene Glycol) on Liposomes and Erythrocytes: Permeability Changes and Membrane Fusion," *Biochimica et Biophysica Acta*, 689:548–560, 1982.

Arnold et al., "The Dielectric Properties of Aqueous Solutions of Poly(Ethylene Glycol) and Their Influence on Membrane Structure," *Biochimica et Biophysica Acta*, 815:515–518, 1985.

Arnold et al., "Effect of Poly(Ethylene Glycol) on Phospholipid Hydration and Polarity of the External Phase," *Biochimica et Biophysica Acta*, 728:121–128, 1983.

Bahnson & Boggs, "Addition of Serum to Electroporated Cells Enhances Survival and Transfection Efficiency," *Biochemical and Biophysical Research Communications*, 171(2):752–757, 1990.

Behr et al., "Efficient Gene Transfer Into Mammalian Primary Endocrine Cells with Lipopolyamine–Coated DNA," *Proceedings of the National Academy of Science USA*, 86:6982–6986, 1989.

METHODS AND COMPOSITIONS OF A POLYMER (POLOXAMER) FOR REPAIR OF ELECTRICAL INJURY

This application is a continuation of application Ser. No. 07/884,429, filed May 15, 1992 now abandoned.

BACKGROUND OF THE INVENTION

I. Field of the Invention

The present invention relates generally to the treatment of electrical injury. The invention is directed to methods and compositions for the treatment of cell membrane damage and tissue injury caused by the disruption of cell membrane integrity following electrical injury. In particular, the invention concerns the treatment of tissue damage and the enhancement of cell survival through the sealing of permeabilized cell membranes by administering an effective amount of a composition comprising a surface-active copolymer, and more preferably, through the co-administration of a surface-active copolymer and a high energy phosphate compound.

II. Background of the Invention

A high percentage of major electrical trauma victims suffer extensive tissue necrosis, high-level amputations and become permanently disabled (DiVincenti et al., 1969). Among electrical utility workers in the United States, the majority of shock victims experience hand-to-hand or hand-to-foot contacts between 6 and 10 kv. Electrical shock simulations by computer suggest that with perfect electrical contacts such circumstances can produce electric field strengths in upper extremity tissues ranging between 60 and 160 V/cm (Tropea & Lee, 1992). Fields of this magnitude can produce skeletal muscle and peripheral nerve membrane damage through electroporation (Lee & Kolodney, 1987b), Joule heating (Lee & Kolodney, 1987a; Lee et al., 1988), or a combination of both.

Skeletal muscle and peripheral nerve necrosis appears to be the primary cause of the high amputation rates associated with electrical trauma. In cases of high-voltage electrical trauma, loss of structural integrity of the cell membrane is believed to be a central pathophysiologic event (Lee & Kolodney, 1987a; Lee & Kolodney, 1987b; DiVincenti et al., 1969; Tropea & Lee, 1992). Membrane damage is often manifested by the release of intracellular contents into the intravascular space, which is, indeed, one of the clinical hallmarks of major electrical trauma. It has been postulated that in the majority of electrical injury victims, cell membrane permeabilization is the most important event in these necrotic processes (Tropea & Lee, 1992; Bhatt et al., 1990; Jaffee, 1928).

'Membrane permeabilization' is the production of discrete openings at numerous sites in cell membranes. The consequences of membrane permeabilization are numerous, and include loss of cytoplasm and some of the contents thereof, disruption of ionic concentration gradients, and depletion of intracellular energy stores. Cells which suffer cell membrane permeabilization may thereafter die and the tissue will subsequently undergo necrosis. One of the consequences of the permeabilization is concomitant egress of the contents of the cell, and without some means of potentiating the repair of the openings, cell survival rates can often be unacceptably low.

One of the more serious consequences of cell membrane permeabilization is the significant depletion of intracellular energy stores. Under normal circumstances, cells maintain a high level of ATP by using oxidizable substrates as sources of free energy. Following permeabilization, a considerable amount of cellular energy would be expended in an attempt to maintain intracellular ionic balances despite the efflux of ions through the permeabilized cell membrane, according to their concentration gradients. During this period of imbalance, the ATP demand will increase to fuel the repair processes, but the intracellular reactions which regenerate ATP stores will be inhibited, leading to a further depletion of the cellular ATP stores. This can render the cell unable to re-establish appropriate ionic gradients across the membrane, prevent it from functioning normally, and ultimately lead to cell death.

A system in which such a depletion of ATP has been well demonstrated is in animals suffering hemorrhagic shock. It has been demonstrated that administration of $ATP-MgCl_2$ before, during, and even after a period of severe shock in rats had a beneficial effect on the animals' survival. The ATP was administered along with the $MgCl_2$ in order to prevent chelation of divalent cations from the vascular system by ATP administered alone. Furthermore, $MgCl_2$ inhibits the deamination and dephosphorylation of ATP. Thus, by administering equimolar amounts of ATP and $MgCl_2$, a higher concentration of ATP will be available to the tissues than if the ATP were administered alone. The results of this study suggested that the beneficial action of $ATP-MgCl_2$ may not have been through vasodilation alone, and it was postulated that the administered ATP could have a "priming effect" on the intracellular synthesis of ATP (Chaudry et al., 1974).

The actual method of cell membrane repair in vivo remains unknown, although researchers have made some inroads toward understanding the mechanisms involved. Calcium ions have been implicated, through both in vitro and in vivo studies, as having a critical role in membrane fusion and repair (Aldwinckle et al., 1982; Papahadiopoulos et al., 1990; McNeil, 1991). Membrane and cytoskeletal proteins, including spectrin, dystrophin, and actin may also be actively involved in the maintenance and repair of the cell membrane in vivo (McNeil, 1991). It has also been suggested that chemical factors may play a signal-like role in wound healing at the cellular level (McNeil, 1991).

Unfortunately, no immediately effective method for treating such injuries currently exists. Also, although methods have been described which reduce the deleterious effects of cell membrane permeabilization, each suffers from particular limitations. The addition of serum to cells permeabilized through the use of electrical pulses has been shown to enhance cell survival (Bahnson & Boggs, 1990). However, serum proteins do not effectively reach damaged cells in vivo. Accordingly, there is a currently lack of a safe and effective method of treating the tissue damage which results from electrical injury.

As membranes form spontaneously when surfactants (amphiphiles) are mixed in an aqueous solvent at sufficient concentration, the inventor hypothesized that it may be possible to seal damaged cell membranes by exposing them to adequate concentrations of a non-cytotoxic non-ionic surfactant.

Several biomedical applications of surface active copolymers, and in particular poloxamers, have been described. These include use as an agent in the preparation of stable and concentrated antiserum, as an emulsifying agent, as a wetting agent in an antiseptic skin cleaning formulation (Rodeheaver et al., 1980), as an enhancer of drug or antibiotic levels in the blood, and as a tool in the study of tumor metastasis (Schmolka, 1977).

Specifically, poloxamer 188 has been used as an emulsifying agent since the 1950s. Initially it was used as a surfactant to protect red blood cells in the membrane oxygenators of early model cardiopulmonary bypass machines, and was shown to prevent hemolysis and lipid embolism. It has been used as an emulsifying agent in foods, oral drugs and cosmetics and is an FDA-approved food additive. Poloxamer 188 has been shown to block the adhesion of fibrinogen to hydrophobic surfaces and the subsequent adhesion of platelets and red blood cells. It is currently an FDA-approved surfactant in the synthetic blood replacement flusol (Check & Hunter, 1988; see also U.S. Pat. Nos. 4,879,109; 4,897,263; and 4,937,070; each incorporated herein by reference.

As mentioned above, there is a particular need for a safe and effective method of treating electrical injury victims. Because cell membrane permeabilization is an important factor leading to tissue necrosis after electrical injury, this suggests that effective therapy for victims of electric shock should re-establish cell membrane structural integrity. A method which addresses the problems of permeabilization and energy store regeneration associated with such an injury would be a particularly novel and advantageous development in this field.

SUMMARY OF THE INVENTION

The present invention is directed to methods and compositions for the treatment of cell membrane damage and tissue injury caused by the disruption of membrane integrity following electrical injury. The invention particularly concerns a method for reducing cellular necrosis and tissue damage through the sealing of permeabilized cell membranes. This is achieved by the administration of an effective amount of a composition comprising a surface-active copolymer, and preferably, through the co-administration of a surface-active copolymer and a high energy phosphate compound.

This invention is based upon recognition of the critical importance of maintaining cell membrane integrity in order to prevent tissue damage, particularly following electrical injury. The invention embodies a collection of methods whereby cell membrane damage can be either minimized or more rapidly repaired through the use of pharmaceutical compositions containing a surface active copolymer, such as a poloxamer. The present invention also recognizes the potential for enhanced recovery of damaged tissue where one desires to re-establish cell membrane integrity as rapidly as possible.

The present invention is thus generally directed to methods of treating electrical injury tissue damage resulting, at least in part, from permeabilization of the membranes of the cells which make up the damaged tissue. The administration of an effective amount of a pharmaceutical composition of a surface active copolymer, and preferably, a poloxamer, constitutes such a method.

Further aspects of the present invention embody the unique realization that high energy phosphate compounds can potentiate the benefits which result from membrane repair by re-establishing cellular energy stores and restoring metabolic functions. In such preferred embodiments, the invention concerns the co-administration of a surface active copolymer in combination with a high energy phosphate compound which can potentiate the healing process. Suitable high energy phosphate compounds are contemplated to be, for example, ATP-$MgCl_2$ or phosphocreatine.

Depending upon the nature of the injury and the copolymer used, the pharmaceutical composition containing the copolymer, or copolymer and high energy phosphate compound, may be administered topically, intravenously, intramuscularly or subcutaneously.

It is contemplated that the surface active copolymer will preferably comprise a poloxamer with a molecular weight of at least 2,000 and not more than 20,000 Daltons. More preferably, the poloxamer's hydrophobic group will have a molecular weight of approximately 950–4,000 Daltons, and its hydrophilic groups will constitute approximately 45–95% by weight of the poloxamer. In a particularly preferred embodiment, the hydrophobic group will have a molecular weight of 1,750–3,500 Daltons, and the hydrophilic groups will constitute approximately 50–90% by weight of the poloxamer. As will be presented in further detail below, the molecular weight of the poloxamer itself and of the hydrophobic group, and the relative weight of the hydrophilic group are critical in determining the physical properties of the poloxamer, the more important of which include its solubility in water and its characteristics when interacting with hydrophobic groups in the cell membrane.

In even more preferred embodiments, it is contemplated that a high energy phosphate compound will be co-administered with the surface active copolymer. This allows for concomitant re-establishment of the cellular energy charge along with repair of the cell membrane, enhancing cell survival following the electrical injury. For example, 1% w/v ATP and 1% w/v $MgCl_2$ may be co-administered with a poloxamer composition. In an alternative preferred embodiment, approximately 10% w/v phosphocreatine, a phosphoric acid derivative of creatine which contains an energy-rich phosphate bond, may be used in place of ATP-$MgCl_2$ as the high energy phosphate compound. Intramuscular injection is also appropriate, with a poloxamer concentration of 1–10% w/v, and, in a preferred embodiment, ATP at a concentration of 1% w/v and $MgCl_2$ at a concentration of 1% w/v, or phosphocreatine at a concentration of approximately 10% w/v.

DETAILED DESCRIPTION OF THE PREFERRED EMBODIMENTS

It has been postulated that the appearance of surfactant molecules on earth several billion years ago was one of the critical events which made life possible (Horgan, 1991). In an aqueous environment surfactants possess the ability to self-assemble into electrically insulating membranes, membranes which permit ionic compartmentalization. Several common, serious illnesses are related to the loss of cell membrane integrity, among them post-ischemic tissue reperfusion injuries, ionizing irradiation injuries, and "burns" of a chemical or thermal nature. Electrical shock injury is the clinical paradigm for these disorders. Advances in clinical medicine over the past two decades have focused on the correction of the physiologic consequences of these injuries at the tissue and organ system level. The next important step is correction of the underlying cytopathology. Progress toward more effective clinical intervention depends upon the development of an effective approach to cell membrane repair.

Victims of major electrical trauma frequently suffer extensive skeletal muscle and nerve damage which is postulated to be mediated partly by cell membrane permeabilization. The present inventor reasoned that effective therapy for victims of electric shock should re-establish cell membrane structural integrity, and preferably, should also provide a means for promoting cellular energy store regeneration. The present invention is therefore directed to a blood-compatible surfactant for sealing electroporated muscle membranes.

In a simplistic model of membrane repair it could be postulated that upon permeabilization (opening at numerous sites) of the cell membrane, both the hydrophobic region of membrane protein and the hydrophobic moieties, tails of the membrane's lipid bilayer are exposed to the more polar, aqueous environments of the extracellular fluid and the cell cytoplasm. Cytoskeletal elements typically located at or near the internal layer of the cell membrane might be expected to react in such a way as to form at least a partial barrier to the escape of intracellular organelles and compartments. However, ions would be expected to both escape from and enter into the cell down their concentration gradients, and other small molecules to pass through the patencies. In fact, if the extent of the damage to the cell membrane were severe, it could be envisioned that a significant amount of cytoplasm, including macromolecules and small organelles, may leak out of the cell.

The lipid molecules in the membrane bilayer nearest the openings would be expected to respond to exposure to the polar environment by reorienting themselves such that their hydrophilic head groups would turn toward the polar solution at the point of exposure. This would isolate the hydrophobic tails of the lipid molecules within the membrane from the aqueous intra- and extracellular space. Membrane fusion and repair of the patencies would occur as the newly formed hydrophilic edges of the patencies move into apposition to each other (Behr et al., 1989). A method whereby such a mechanism could be potentiated, especially if the method provided the means for restoring the permeabilized cells' energy charge, would represent an important advance in the treatment of injuries involving cell membrane permeabilization.

Surface active copolymers, or block polymer nonionic surfactants, are surface active agents prepared by the sequential addition of two or more alkylene oxides to a low molecular weight water soluble organic compound containing one or more active hydrogen atoms. There are four groups of surface active copolymers of particular importance with regard to the present invention: the poloxamers, the meroxapols, the poloxamines and the PLURADOT® polyols. There is a certain amount of intergroup variation with respect to the polymer's synthesis, although in all syntheses the oxyalkylation steps are carried out in the presence of an alkaline catalyst, generally sodium or potassium hydroxide. The alkaline catalyst is then neutralized and typically removed from the final product.

The poloxamers are synthesized by the sequential addition of propylene oxide, followed by ethylene oxide, to propylene glycol, which in the case of the poloxamers constitutes the water-soluble organic component of the polymer. The inner polyoxy-propylene glycol is the hydrophobic portion of the poloxamer. This is due to the fact that this group changes from a water-soluble to a water-insoluble polymer as the molecular weight goes above 750 Daltons. Adding ethylene oxide in the final step makes the molecule water-soluble.

In preferred embodiments, the invention contemplates the use of a poloxamer with a molecular weight of at least 2,000 and not more than 20,000 Daltons. This molecular weight range is important in maintaining the appropriate solubility of the poloxamer in water while minimizing or eliminating any potential toxicity. Furthermore, the poloxamer's hydrophobic group should have a molecular weight of approximately 950–4,000 Daltons, and its hydrophilic groups should constitute approximately 45–95% by weight of the poloxamer. More preferably, the hydrophobic group should have a molecular weight of 1,750–3,500 Daltons, and the hydrophilic groups should constitute 50–90% by weight of the molecule. As will be discussed in greater detail below, the relative amounts of hydrophile and the molecular weight of the hydrophobe are critical to several of the poloxamer's properties, including its solubility in water and its interactions with hydrophobic groups, and the ranges taught in the present invention provide the maximum effectiveness currently known while minimizing or eliminating toxicity.

When the order of addition of the alkylene oxides is reversed, the meroxapol series is produced. In this series, ethylene glycol is the initiator, and as opposed to the poloxamers, which are terminated by two primary hydroxyl groups, the meroxapols have secondary hydroxyl groups at the ends and the hydrophobe is split in two, each half on the outside of the surfactant.

The poloxamines are prepared from an ethylene diamine initiator. They are synthesized using the same sequential order of addition of alkylene oxides as used to synthesize the poloxamers. Structurally, the poloxamines differ from the other polymers in that they have four alkylene oxide chains, rather than two, since four active hydrogens are present in the initiator. They also differ from the other surfactants in that they contain two tertiary nitrogen atoms, at least one of which is capable of forming a quaternary salt. The poloxamines are also terminated by primary hydroxyl groups.

The PLURADOT® polyols can be prepared from a low molecular weight trifunctional alcohol, such as glycerine or trimethylpropane, which is oxyalkylated initially with a blend of propylene and ethylene oxides, but primarily with propylene oxide, to form the hydrophobe. This is followed by oxyalkylating with a blend of ethylene and propylene oxines, but primarily ethylene oxide, to form the hydrophile. This group of surfactants has three chains, one more than the poloxamer and meroxapol series, but one less than the poloxamine polymers.

The hydrophilic and hydrophobic chains of the surface active copolymers each have unique properties which contribute to the substances' biological activities. With regard to poloxamers in particular, the longer the hydrophilic polyoxyethylene chains are, the more water the molecule can bind. As these flexible chains become strongly hydrated they become relatively incompressible and form a barrier to hydrophobic surfaces approaching one another. The hydrophobic component of the poloxamers is typically large, weak and flexible.

In any of the surface active copolymer series, as the percent of ethylene oxide increases, or the molecular weight of the hydrophobe decreases, the solubility of the molecule in water increases. Of the four groups of copolymers only the meroxapol polymers exhibit any solubility in mineral oil. The higher the hydrophobic molecular weights, the less soluble the copolymer will be in an organic solvent, and the same is true for those polymers with higher ethylene oxide or propylene oxide concentration. The molecular weight of the hydrophobe will also affect the wetting time of any one species, and the ethylene oxide/propylene oxide ratio of the molecule will influence the foaming properties of that copolymer. A copolymer's emulsification properties may correlate with hydrophobe molecular weights, and toxicity decreases as the ethylene oxide/propylene oxide ratio increases and as the molecular weight of the hydrophobe increases.

All four nonionic series are alike in that they derive their solubility in water from hydrogen bond formation between the many oxygen atoms on the copolymer and protons in the water. As the temperature of a solution containing a nonionic surfactant is raised, the hydrogen bonds are broken and the copolymer clouds out of solution. For example, for poloxamers the 1% cloud point ranges from a low of 14° C. to a high of 100° C., the latter figure being the cloud point for the most hydrophilic polymers. The poloxamines are similar structurally to the poloxamers, and their cloud point range is similarly wide. On the other hand, the meroxapols have a much narrower cloud point range, and the PLURADOT polymers have the lowest maximum cloud point, primarily due to their lower ethylene oxide content.

Although others have postulated that the ability of the modified poloxamer 188 to form single molecule micelles may play a role in reducing the adhesive properties of damaged cell membranes, the current invention is the first to recognize that surface active copolymers are capable of preventing or minimizing cell membrane permeabilization and repairing permeabilized membranes. It has been suggested that the hydrophobic central domain of the polymer may bind to the hydrophobic portions of the lipid bilayer when these groups are exposed following removal of the external layer of the membrane. The manner in which the poloxamer is folded when this binding occurs has been postulated to assist in the restoration of a non-adhesive cell surface. However, the present invention recognizes that poloxamers are surprisingly capable not merely of restoring a non-adhesive surface, but actually of repairing or potentiating the repair of complete permeations of the entire membrane bilayer.

The present inventor has determined that the synthetic surfactant, poloxamer 188 (P188), which has been clinically accepted for human intravenous administration, effectively seals electroporated membranes of cultured skeletal muscle cells when used in concentrations greater than 0.5 mg/ml. Furthermore, membrane sealing was observed to enhance cell survival, as measured by vital dye (i.e., carboxyfluorescein and trypan blue) assays.

The in vivo studies described herein further demonstrate that P188 has specific molecular actions distinct from neutral polysaccharides which are known to adsorb to the lipid bilayer of cell membranes (Minetti et al., 1979), and to induce cell aggregation (Brooks & Seaman, 1972). P188 is herein shown to reach damaged cell membranes in situ via intravenous administration and seal them following electropermeabilization. Most importantly, this membrane sealing effect is shown to prevent tissue necrosis following electrical injury.

For clinical use, injection of a pharmaceutical composition comprising a sterile filtered poloxamer in a suitable pharmacological carrier at a dose of between 0.1 mg per ml of blood volume to 5 mg per ml of blood volume is expected to result in rapid reversal of cell membrane permeabilization following electrical injury. In preferred embodiments, it is contemplated that the poloxamer will have a molecular weight of at least 2,000 but not more than 20,000 Daltons; the total molecular weight of the hydrophobe will be approximately 950–4,000 Daltons; and the hydrophilic groups will constitute approximately 45–95% by weight of the poloxamer. More preferably, the hydrophobe will have a molecular weight of approximately 1,750–3,500 Daltons; the hydrophilic groups will constitute approximately 50–90% by weight of the poloxamer.

In even more preferred embodiments, a high energy phosphate compound, such as, for example, 1% w/v ATP and 1% w/v $MgCl_2$ will be co-administered with the poloxamer. This allows for concomitant re-establishment of the cellular energy charge along with repair of the cell membrane, enhancing cell survival following the electrical injury. In an alternative preferred embodiment, approximately 10% w/v phosphocreatine, a phosphoric acid derivative of creatine which contains an energy-rich phosphate bond, may be used in place of ATP-$MgCl_2$ as the high energy phosphate compound. Intramuscular injection is also appropriate, with a poloxamer concentration of 1–10% w/v, and, in a preferred embodiment, ATP at a concentration of 1% w/v and $MgCl_2$ at a concentration of 1% w/v, or phosphocreatine at a concentration of approximately 10% w/v.

For topical administration, the poloxamer is presented in a pharmacologically appropriate substrate at a concentration of 1–10% w/v, and in a preferred embodiment, ATP and $MgCl_2$ are present along with the poloxamer at an appropriate concentration of 1% w/v and 1% w/v respectively. Phosphocreatine at a concentration of approximately 10% w/v could be used as an alternative to ATP and $MgCl_2$. The sterile substrate containing the poloxamer and high energy phosphate compound is applied to the damaged area, wrapped as appropriate with sterile dressings, and is reapplied as necessary. Either topical administration or intravenous administration could be supplemented as necessary with the other form of administration in cases where dual administration is required.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

SEALING OF ELECTROPERMEABILIZED SKELETAL MUSCLE MEMBRANES IN VIVO

A. Materials and Methods

1. In Vitro Muscle Cell Membrane Sealing

The efficacy of poloxamer in membrane sealing was initially analyzed using isolated rat skeletal muscle cells, and compared to dextran or saline controls. Skeletal muscle cells were harvested by 0.1% collagenase (Type II, Sigma Chemical Co., St. Louis) in phosphate-buffered saline (PBS) digestion at 37° C., washed extensively with 10% horse serum supplemented PBS and maintained in culture (Bhatt et al., 1990; Bischoff, 1986). The cells were maintained under physiologic conditions in Dulbecco's Modified Eagles' Medium (DMEM) supplemented with 20% calf serum and 2× penicillin/streptomycin until used experimentally after 48 to 72 hours.

Figure 1:
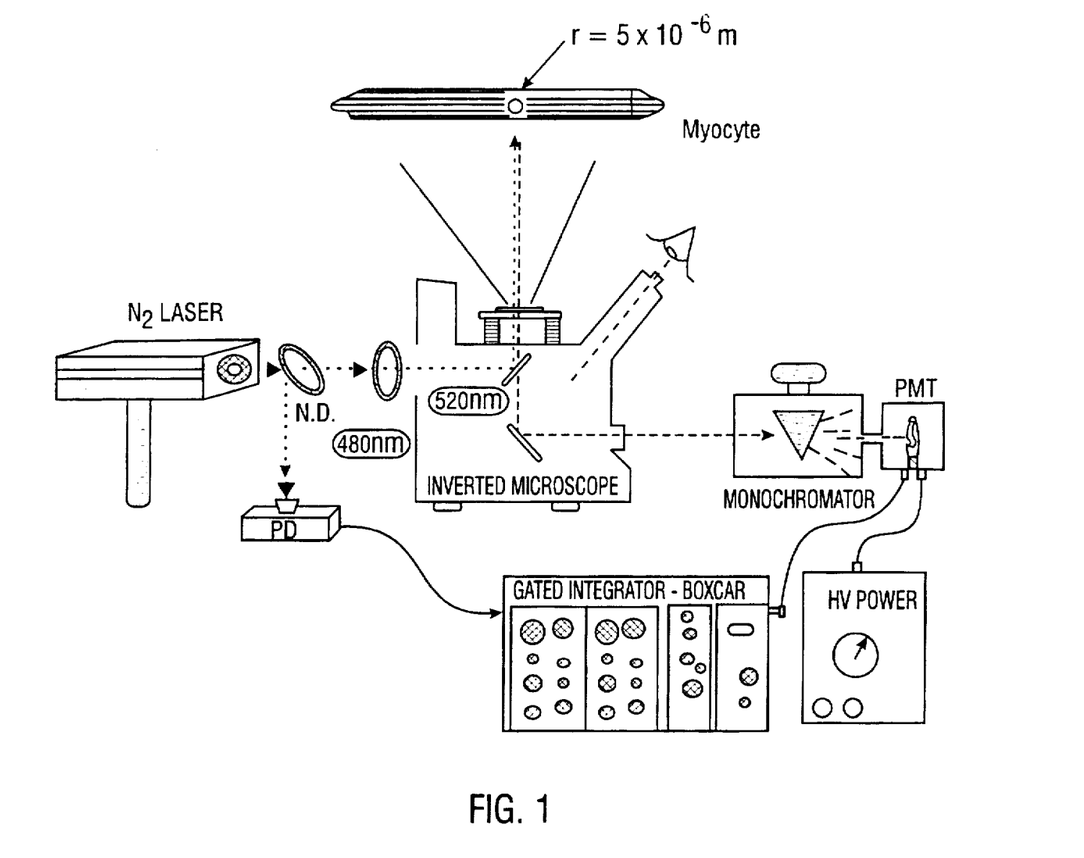
FIG. 1: Apparatus used to measure membrane permeability on isolated rat skeletal muscle cells [N.D.—Neutral Density filter; PD—photodetector; PMT—photomultiplier tube].

In order to load the cytoplasm with a membrane impermeant dye, the cells were preincubated in $Ca^{++}$-free PBS containing 1.5 mM $MgCl_2$, 25 mM Hepes buffer, and 20 µM carboxyfluorescein diacetate (CFDA) for 2 hours. They were then incubated in the same solution without CFDA for 30 minutes prior to transfer to a custom microscope stage chamber (Bhatt et al., 1990) containing the buffered $Mg^{++}$-PBS and aligned perpendicular to the direction of current passage. Carboxyfluorescein content in these 1000×30 micron (average length×diameter) rat flexor digitorum brevis skeletal muscle cells (n=6) was measured by digital video data microfluorometry. The intracellular carboxyfluorescein (CF) was excited at ($\lambda_{ex}=$) 480 nm. The emission at ($\lambda_{em}=$) 520 nm was converted to standard RS170 video format (30 frames/second) with an intensified Hamamatsu Neuvicon camera and its output was digitized (512×512×16 bits) using a Hamamatsu C1966 image processor linked by Direct Memory Access (DMA) to a DEC VAX Station II computer (Digital Equipment Co., Maynard Mass.) (FIG. 1).

Each data frame consisted of an average of 16 sequential frames. Gaussian filters were used to perform shading correction, after which the intracellular pixels were normalized to the mean background level; the background fluorescence value was then subtracted from the entire frame by digital image processing methods. A computer controlled shutter (AZI Model) blocked the excitation beam between measurements to minimize cellular phototoxic effects. The excitation intensity was lowered with different neutral density filters to the level at which photobleaching did not produce detectable fluorescence emission loss over a 10 minute interval.

Intracellular CF monitoring began at t=0 minutes; the cell was then exposed to a single 200 volt/cm, 4-ms duration field pulse (E in FIG. 2) at t=5 minutes. Data frames were collected at 1 minute intervals. This procedure was repeated using PBS supplemented with either 8 mg/ml neutral dextran (10.1 kDa, Sigma Chemical, St. Louis, Mo.) or 8 mg/ml P188 (BASF Corp., Parsippany, N.J.) in the medium bathing the cells (n>5).

2. In Vivo Muscle Tissue Impedance Responses

Figure 3:
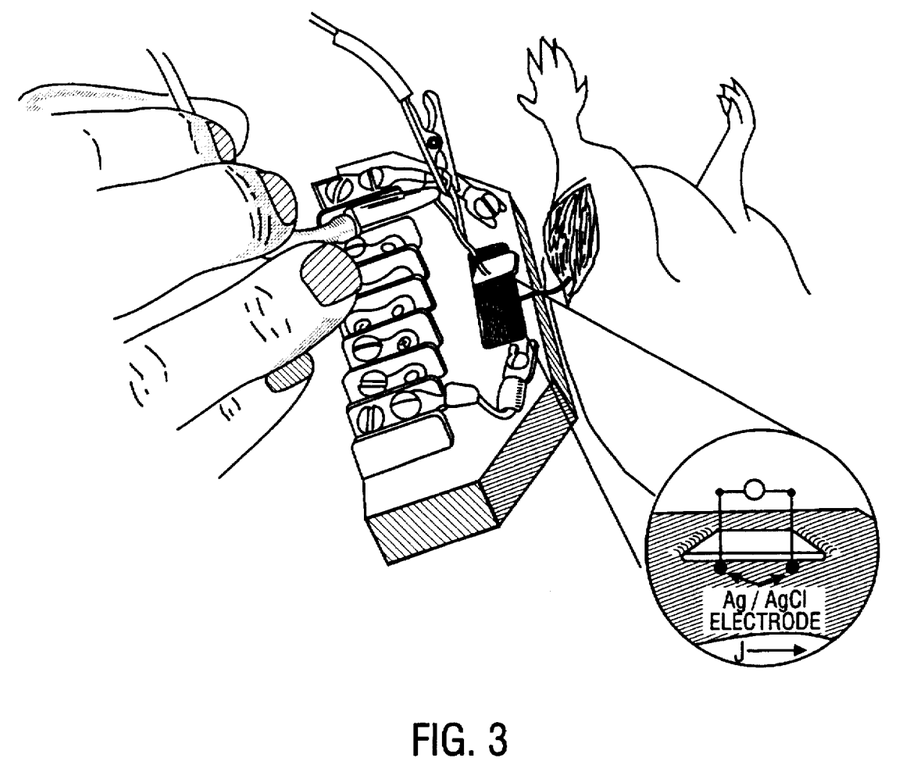
FIG. 3: Apparatus for measuring muscle impedance magnitude (@100 Hz) with the rat biceps femoris island muscle flap in the apparatus.

Male Sprague-Dawley rats weighing 275–375 grams were anesthetized using intraperitoneal ketamine (100 mg/kg) and xylazine (13 mg/kg). A biceps femoris muscle flap with an intact arteriovenous pedicle was developed (FIG. 3). The cells in this muscle range between 2–3 mm in length with diameters between 20–50 microns (Jaffee, 1928). Care was taken to keep the tissue moist and to avoid surgical damage to the muscle cells. Continuous blood flow through the vascular pedicle was confirmed throughout each experiment by microscopic examination.

The low-frequency (<1.0 kHz) electrical impedance of skeletal muscle is sensitive to cell membrane integrity (Bhatt et al., 1990; Chilbert et al., 1985). The electrical impedance of the flap was measured as described by Bhatt et al. (1990). To measure membrane resistivity, the muscle flap was placed in an electrically insulating 2 (length)×1 (width)×1.5 (depth) cm chamber within a polysulfonate block constructed for making two-port electrical impedance measurements. Immediately prior to impedance measurement, excess buffer was blotted from the muscle surface, and the cross-section of the muscle flap was measured.

A Wavetek® function generator (model 191, Wavetek® Corporation, San Diego, Calif.) and a Kepco® Inc. bipolar operational amplifier (model BOP 200-1M, Flushing, N.Y.) configured as a current source were used to establish a 100 Hz sinusoidal one milliamp (peak) current. Two Ag/AgCl electrodes mounted five millimeters apart in an epoxy block were centrally placed on the muscle surface to measure the voltage gradient. The potential difference between the Ag/AgCl electrodes was measured by a FET differential amplifier (Tektronic® model 11A33) module in a Tektronix digital oscilloscope (model 11401, Beaverton, Oreg.) configured as an impedance spectrometer. The value of the flap impedance magnitude parallel to the muscle cell orientation, minus the impedance of PBS, was calculated, corrected for the cross-section, normalized to its initial value, and used as an index for membrane damage (Bhatt et al., 1990; Canaday & Lee, 1990).

After three baseline impedance determinations, sufficient isotonic phosphate-buffered saline (PBS) with 50 mM Hepes buffer was added to cover the muscle and permit a uniform electric field. Sixty unipolar, rectangular, one-ampere current pulses, each four milliseconds in duration, induced a 150-volts/cm electric field in the chamber. A 10-second duty cycle was set to minimize temperature elevation. The added PBS was then removed and post-shock muscle impedance was monitored again. The cross-section of the muscle flap was measured before and after the electrical shock and used to calculate resistivity.

Treatment and control intravenous injections were administered 20 minutes post-shock into the contralateral femoral vein under microscopic visualization. Treated animals received bolus injections of 460 mg/kg P188 dissolved in 1.8 ml of isotonic saline. Control animals received either 460 mg/kg neutral dextran dissolved in isotonic saline or an equivalent volume of isotonic saline. Poloxamer and dextran injections were randomized and coded so that their identity was not known to the experimenter. All preparations were filter-sterilized. For each group, the mean and standard error of the mean (SEM) of the normalized resistivity (i.e., impedance corrected for cross-section and normalized to the pre-shock value) were calculated. This protocol was carried out according to institutional guidelines for animal care. Statistical comparisons between sample means were made using the Wilcoxon signed-rank test for non-parametric data, with the null hypothesis that the means were identical.

Baseline tests were conducted to determine the effects of bath conditions and intravenous injections on the resistivity. Resistivity measurements were made every 30 minutes for two hours on untreated animals, and on animals which had received P188, neutral dextran, or isotonic saline. Dosages were designed to yield a peak blood level of 8 mg/ml.

Joule heating-related temperature changes were estimated by measuring bath temperature. A calibrated thermistor was centrally placed in the chamber which was packed with surgical gauze (surgical gauze has a dc resistivity similar to skeletal muscle) and soaked with isotonic PBS with 50 mM Hepes buffer. The temperature was taken every 10 pulses up to 60 pulses. The pH of the bath was determined using litmus paper pre-calibrated against a Corning® pH meter.

3. In Vivo Response Kinetics

To gain insight into the dose-dependence of the in vivo membrane sealing, experiments were performed in which several different dosages of P188 was injected intravenously 10 minutes prior to the electropermeabilization of the flap. The flap and the impedance measurement was set up as described above. Impedance was monitored at 5-minute intervals using the methods previously described.

4. Post-Injury Tissue Survival

Further studies were conducted to examine the effect of P188 on muscle survival under electrical exposure conditions simulating accidental electrical shock. In these studies the skin overlying the flexor digitorum brevis (FDB) muscle of the hind foot was raised as a flap to expose the muscle. The foot was immersed in the chamber previously described, saline was added to cover the foot, and a 150-volts/cm 60-Hz sinusoidal current was applied for 5 seconds. Either P188 or an equivalent volume of isotonic saline was injected intravenously 15 minutes post-shock, using doses identical to those used in resistivity studies. The peak temperature of the bath immediately following current cessation was recorded using a calibrated thermistor. The flap was closed with sutures and cyanoacrylate glue and the foot placed in a bulky dressing. At 4 and 24 hours post-shock each animal was again anesthetized and additional intravenous doses of either P188 or isotonic saline were given. Seventy-two hours later the animal was sacrificed and the FDB muscle was removed and fixed in neutral-buffered formalin.

B. RESULTS

1. CF Membrane Permeation

Skeletal muscle cells isolated from the flexor digitorum brevis muscle ranged from 800 to 1200 microns in length and 25 to 30 microns in diameter, which is in accordance with previously described results (Lee et al., 1988; Gaylor, 1989). Such muscle cells were observed to maintain their normal sarcoplasmic striations and shape in culture. The viability of the cells was affirmed by the intracellular incorporation and catalysis of CFDA to its fluorescent form, CF.

Figure 2:
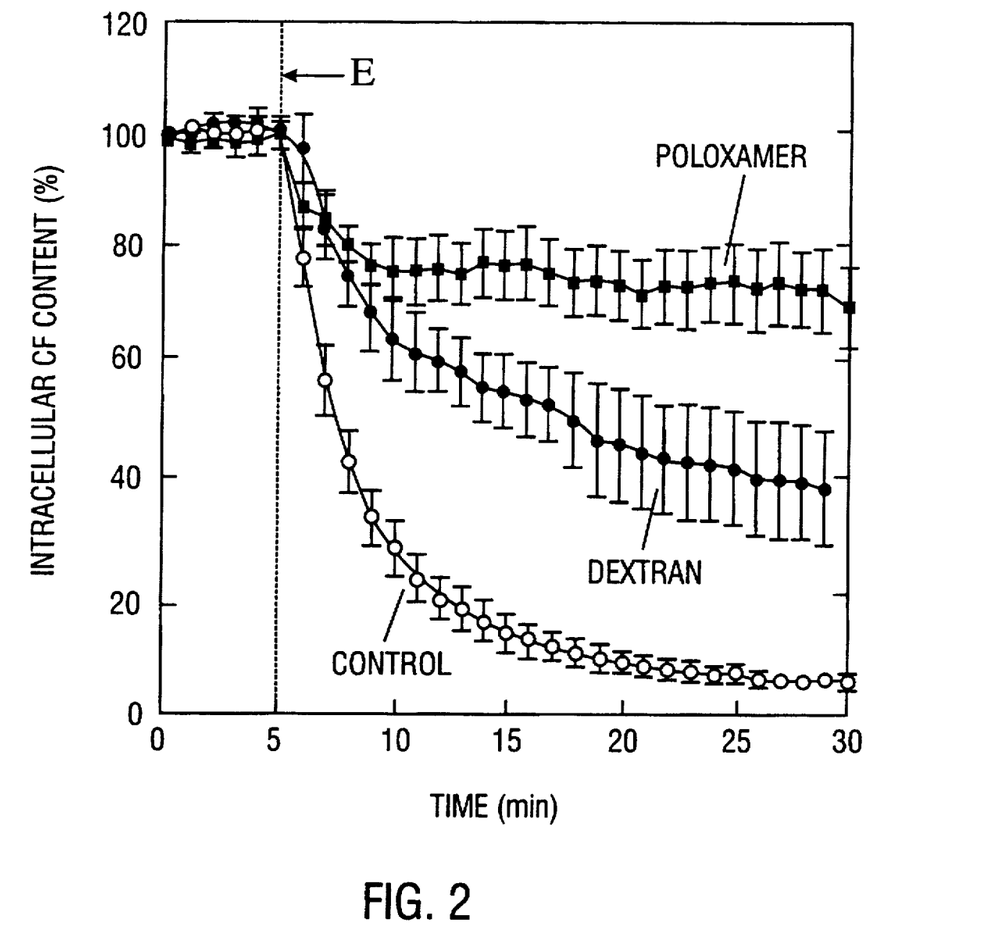
FIG. 2: Carboxyfluorescein release from isolated 1000× 30 micron (average length×diameter) rat flexor digitorum brevis skeletal muscle cells (n=6) following a single 200 volt/cm, 4-ms duration field pulse. The cells were preincubated in $Ca^{++}$-free PBS with 1.5 mM $MgCl_2$, 25 mM Hepes buffer, and 20 µM carboxyfluorescein diacetate (CFDA) for 2 hours. The cells were then incubated in the same solution without CFDA for 30 minutes, transferred to a custom microscope stage chamber (Bhatt et al., 1990) containing the buffered $Mg^{++}$-PBS, then exposed to field pulse. The field pulse (E) was delivered at t=5 minutes. The intracellular carboxyfluorescein was excited at 480 nm and the emission at 520 nm was quantified by digital imaging processing methods as described by Ji & Lee (1990). The procedure was repeated using PBS supplemented with either 8 mg/ml neutral dextran (10.1 kDa, Sigma Chemical, St. Louis, Mo.), or 8 mg/ml poloxamer 188 (BASF Corp., Parsippany, N.J.).

A single 4-millisecond duration field pulse electropermeabilized the 100% of the test cells. This was manifested by a loss of dye from the cell (FIG. 2). In control cells the dye loss kinetics exhibited a single exponential decay with a characteristic time constant of approximately 284 seconds. For cells bathed in either P188 or dextran the step increase in membrane permeability observed immediately following the field pulse was followed by a smooth reduction in the slope of the dye loss curve. For the dextran treated cells the slope approached but never reached the pre-shock (near-zero) level. However, the dye loss rate from P188 treated cells return to the near-zero value. In effect, it was observed that P188 or low-molecular-weight (11-kDa) neutral dextran retarded CF release from electropermeabilized rat muscle cells. Further, while dextran retarded CF loss, 8 mg/ml P188 completely arrested transmembrane CF flux.

2. Tissue Impedance Responses

Figure 4:
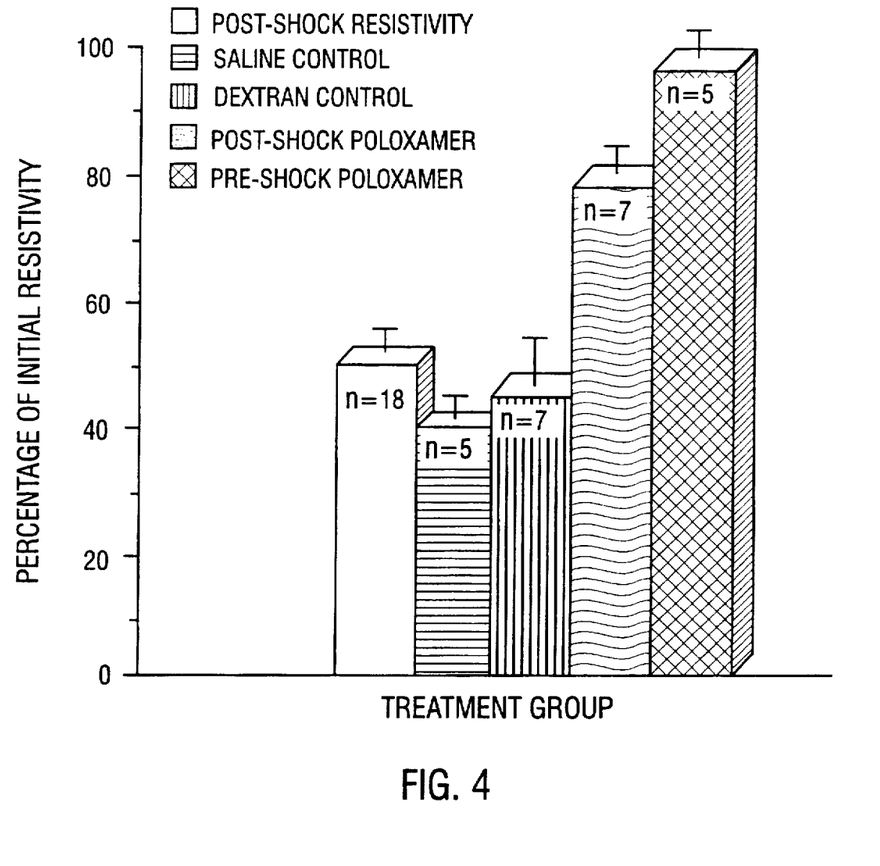
FIG. 4: Normalized resistivity for flaps immediately post-electroporation. Treatment groups shown are: one hour following intravenous saline infusion, one hour following intravenous dextran infusion, one-hour following intravenous poloxamer infusion, and immediately post-electroporation in animals pretreated with poloxamer.

Exposure to the electric field pulses used in this study caused an abrupt and substantial fall in muscle tissue resistivity values (FIG. 4). The resistivity drop averaged 49.9±3.6% (mean±standard error of mean) of initial values. Treatment with intravenous P188 was found to restore flap resistivity to 77.4±4.8% of initial values; which change was statistically significant ($p<0.05$). Intravenous treatment with neutral dextran or isotonic saline had no effect on resistivity values (44.8±8.3% and 39.0±3.0%, respectively, $p>0.1$ in both cases). The resistivity changes seen after P188 treatment occurred within 15 minutes of administration and resistivity was stable for at least two hours. No significant spontaneous changes in resistivity were observed in post-shock control animals which were monitored for two hours (n=5).

In animals pre-loaded with 8 mg/kg P188 (n=5), post-shock flap resistivity averaged 96.3±1.8% of initial values ($p>0.1$) (FIG. 4). Baseline studies were conducted to determine the effects of bath conditions and intravenous injections on the resistivity. Resistivity measurements were made every 30 minutes for two hours on untreated animals, and on animals which had received P188, neutral dextran, or isotonic saline. Dosages were designed to yield a peak blood level of 8 mg/ml. No significant spontaneous changes in flap resistivity were observed in unshocked, untreated animals or in unshocked animals receiving intravenous P188, neutral dextran, or isotonic saline.

Bath temperatures increased by less than 1.5° C., and no pH changes in the bath medium were detected during or after the electric shock series of 60 pulses. Temperature studies made during actual muscle flap electric field exposure yielded identical results.

Figure 5:
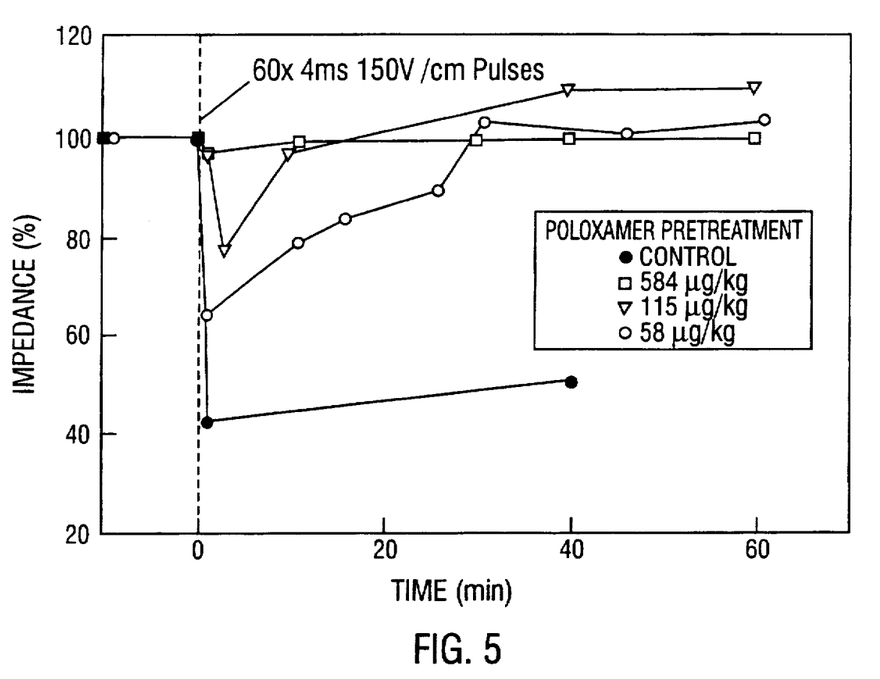
FIG. 5: Plot of membrane impedance versus time for four experiments at t=0; 60 field pulses (shocks) were given, separated by 10 seconds. Muscle impedance was recorded before and after the shocks were administered.

The kinetic response for a range of P188 dosages were also determined. Animals pre-loaded with saline did not demonstrate spontaneous recovery over a one-hour period (FIG. 5). In contrast, all P188 pre-loaded animals manifested complete membrane sealing following electropermeabilization, and the rate of membrane sealing was dose-dependent (FIG. 5).

3. Effect on Post-shock Survival

For the flexor digitorum brevis muscle studies, a 100-volts/cm (peak) sinusoidal ac current was passed for 5 seconds through a bath containing the rat hind foot; the plantar skin was open as a flap exposing the flexor digitorum brevis. Bath temperature peaked at 5 seconds (when the current was turned off), with an average change of 16° C. (reaching a maximum of 37° C.). Within 24 hours after electrical shock there was a readily detectable difference in tissue swelling between control and P188 treated animals. P188 treatment substantially reduced tissue edema, suggesting a reduction in inflammation.

Figure 6A:
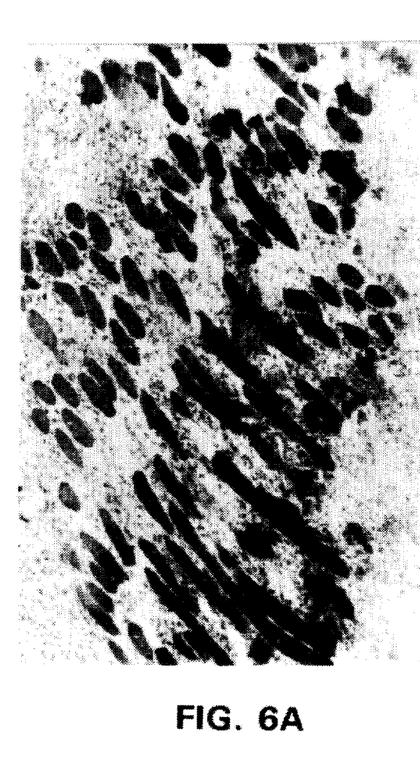
FIG. 6: Histophotomicrograph of skeletal muscle which received electrical shock and was then treated (a) by intravenous saline injection; and (b) by P188 administration; bars=100 μm.
Figure 6B:
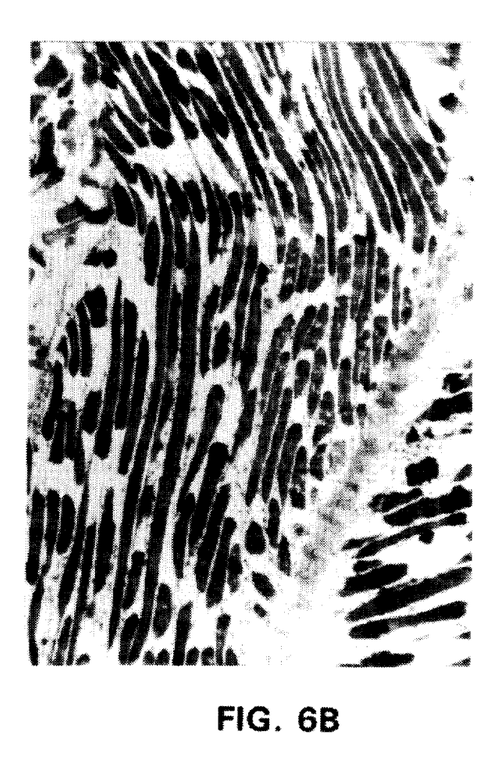

The histomorphology of poloxamer-exposed and control muscle, as assessed in photomicrographs following H & E staining, was markedly distinct (FIG. 6). The architecture of the P188 exposed muscles (FIG. 6b) was significantly less edematous, and has fewer inflammatory changes in comparison with saline-exposed tissue (FIG. 6a). The morphology and extent of changes in the P188 treated group were similar to those observed in tissue adjacent to a surgically closed wound. The intracellular matrix of the poloxamer-treated group of muscle cells appears to be intact, while the cells in saline-treated tissue are fewer in number and show evidence of extensive damage.

As described immediately above, intravenous administration of P188 was found to be effective for delivering the surfactant to the muscle cell membrane. It restored membrane integrity to isolated muscle cells and to 77% of pre-shock values within intact tissue. Loss of intracellular material with concomitant cell shrinkage (DiVincenti et al., 1969) and disruption of the histoarchitecture (Jaffee, 1928) may explain the incomplete recovery in vivo. This explanation is consistent with the absence of a permanent resistivity drop in animals which were preloaded with P188 because membrane sealing would have occurred rapidly preventing any loss of intracellular content.

P188 administration was effective in reducing tissue damage resulting from electropermeabilization of flexor digitorum brevis cell membranes. Histologic evidence of muscle inflammation and damage was still evident, although substantially less than that seen in control animals. The presence of inflammation despite P188 administration may be the result of surgical injury during the surgical manipulation of the skin flaps or perhaps because of non-uniformity in the delivery of P188 to the muscle.

The present results represent the first report of in vivo repair of damaged cell membranes. It now appears that a direct approach exists for the treatment of illnesses which are primarily related to cell membrane damage, setting the stage for the development of effective medical therapy for victims of high-voltage electrical shock.

EXAMPLE II

HUMAN TREATMENT PROTOCOLS

The following example discloses methods of treatment for a human subject suffering from an electrical injury. In certain embodiments, it is proposed that 0.1–5 mg/ml blood volume of sterile, Millipore filtered poloxamer 188 or 1107 (available from BASF Co., Parsippany, N.J.) or RheothRX™ (a formulation of poloxamer 188 available from CytRx® Corp., Atlanta, Ga.) in a pharmaceutically appropriate carrier (e.g., sterile water or buffered saline) would be injected either into a suitable vein, or intramuscularly. Administration may repeated daily as appropriate depending upon the severity of the injury and the response of the individual to the poloxamer treatments.

It is considered to be even more advantageous to administer the polymer with a high energy phosphate compound such as 1% w/v ATP and 1% w/v McCl$_2$, or 10% w/v phosphocreatine, so that the healing of any membrane damage which might have occurred can be potentiated through the recharging of cellular energy stores.

Alternatively, 1 to 10% w/v poloxamer 188 or 1107 may be suspended in a pharmaceutically appropriate sterile ointment (e.g., an oil-in-water type emulsion base) or in sterile water in an aerosol container for direct topical application to the injured tissue. The site of injury would then be bandaged with appropriate dressings and the poloxamer suspension reapplied as necessary, for example, up to six times per day every four hours. In addition, the poloxamer suspension for topical application could also contain a high energy phosphate compound for recharging of cellular energy stores and further potentiation of cell repair. Phosphocreatine (10% w/v) or ATP (1% w/v) and MgCl$_2$ (1% w/v) are examples of preferred high energy phosphate compounds. Depending upon the severity and depth of the tissue injury, the poloxamer and high energy phosphate compounds could be coadministered to the same patient both parenterally and topically. In this way, deep tissue injuries can be treated through parenteral administration, and surface lesions treated directly by topical application. Dose and application regimen need not be varied in cases where oral application is indicated.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background, or teach methodology, techniques, and/or compositions employed herein.

Aldwinckle et al., "Effects of Poly(ethylene glycol) in Liposomes and Erythrocytes Permeability Changes and Membrane Fusion," *Biochem. Biophys. Alta* 689:548–560 (1982).

Bahnson & Boggs, "Addition of Serum to Electroporated Cells Enhances Survival and Transfection Efficiency," *Biochem. Biophys. Res. Comm.* 171:752–757 (1990).

Behr et al., "Efficient Gene Transfer into Mammalian Primary Endocrine Cells with Lipopolyamine-coated DNA," *Proc. Nat'l. Acad. Sci.* 86:6982–6986 (1989).

Bhatt et al., *Plast. Reconstr. Surg.* 86(1):1–11 (1990).

Bischoff, *Developmental Biol.* 115:129–139 (1986).

Brooks & Seaman, Nature(London), *New Biol.* 238:251 (1972).

Canaday & Lee *J. Cell Biol.* 111(5):431a (1990).

Chaudry et al., "Effect of Adenosine Triphosphate-Magnesium Chloride Administration in Shock," *Surgery* 75:220–227 (1974).

Check & Hunter, "The Scientific Basis for the Biologic Activities of RheothRx™ Copolymer: A Rheologic, Antithrombotic and Cytoprotective Preparation," CytRx Corp., 1988.

Chilbert et al., *J. Trauma* 25:209–215 (1985).

DiVincenti et al., *J. Trauma* 9:497–507 (1969).

Gaylor, Ph.D. Thesis, Massachusetts Institute of Technology (1989).

Horgan, *Sci. Amer.* 264(2):117 (1991).

Jaffee, *Arch. Pathol.* 5:837–870 (1928).

Ji & Lee, *J. Cell Biol.* 111(5):431a (1990).

Lee et al., *J. Surg. Res.* 44(6):709–719 (1988).

Lee & Kolodney, *Plast. Reconstr. Surg.* 80:663–671 (1987a).

Lee & Kolodney, *Plast. Reconstr. Surg.* 80:672–679 (1987b).

McNeil, "Cell Wounding and Healing," *Am. Scientist* 79:222–235 (1991).

Minetti et al., *Biochemistry* 18(12):2541–2548 (1979).

Papahadiopoulos et al., "Molecular Mechanisms of Calcium-Induced Membrane Fusion," *J. Bioenergetics*

*Biomembranes* 22:157–179 (1990).

Rodeheaver et al., *Ann. Emerg. Med.* 9:572–576 (1980).

Schmolka, "A Review of Block Polymer Surfactants," *J. Am. Oil Chemists' Soc.* 54:110–116 (1977).

Tropea & Lee, *J. Biomech. Eng.* (in press) (1992).

What is claimed is:

1. A method of reducing animal tissue damage due to electrical injury comprising treating the affected tissue topically with a composition consisting essentially of an amount of a surface active copolymer, selected from the group consisting of a poloxamer, meroxapol, poloxamine and PLURADOT® polyol, that is effective to reduce damage to the tissue by stabilizing cellular membranes or reducing membrane permeability, the surface active copolymer having a molecular weight of between about 2,000 and about 20,000 Daltons and from about 45 % to 95 % hydrophobic groups by weight of the copolymer; in a pharmaceutically acceptable topical vehicle, wherein the composition is administered topically to the electrically injured tissue.

2. A method of reducing animal tissue damage due to electrical injury comprising treating the affected tissue by administering intravenously or intramuscularly to the animal a composition comprising an effective amount of a surface active copolymer, selected from the group consisting of poloxamer, meroxapol, poloxamine and PLURADOT® polyol, the amount being effective to reduce damage to the tissue by stabilizing cellular membranes or reducing membrane permeability, the surface active copolymer having a molecular weight of between about 2,000 and about 20,000 Daltons and from about 45 % to 95 % hydrophobic groups by weight of the copolymer; in a pharmaceutically acceptable intramuscular or intravenous vehicle, wherein the composition is administered intramuscularly or intravenously to the electrically injured tissue.

3. The method of claim 1, wherein the composition consists essentially of about 1% to about 10% (w/v) of the copolymer.

4. The method as in claims 1 and 2, wherein the poloxamer has the general formula:

wherein, a is an integer such that the hydrophobe represented by $(C_3H_6O)_a$ has a molecular weight of approximately 950 to 4,000; and b is an integer such that the hydrophile represented by $(C_2H_4O)_b$ constitutes approximately 45% to 95% by weight of the poloxamer.

5. The method of claim 4, wherein the poloxamer has the general formula:

wherein, a is an integer such that the hydrophobe represented by $(C_3H_6O)_a$ has a molecular weight of approximately 1,750 to 3,500, and b is an integer such that the hydrophile represented by $(C_2H_6O)_b$ constitutes approximately 50% to 90% by weight of the poloxamer.

6. The method of claim 1, wherein said composition further comprises a high-energy phosphate compound.

7. The method of claim 6, wherein the high energy phosphate compound comprises ATP-$MgCl_2$.

8. The method of claim 6, wherein the high energy phosphate compound comprises phosphocreatine.

9. The method as in claims 1 or 2, wherein the animal is a human subject.

10. The method of claim 2 wherein when the composition is administered intravenously it is administered in a dose that is effective to deliver from about 0.1 mg of the copolymer per milliliter of blood volume to about 5 milligram per milliliter of blood volume, and when the composition is administered intramuscularly the administered composition comprises from about 1% to about 10% weight of copolymer to volume of composition.

* * * * *